(12) United States Patent
Uckelmann

(10) Patent No.: US 8,502,107 B2
(45) Date of Patent: Aug. 6, 2013

(54) METHOD AND APPARATUS FOR MAKING PRODUCTS BY SINTERING AND/OR MELTING

(75) Inventor: Ingo Uckelmann, Bremen (DE)

(73) Assignee: BEGO Medical GmbH (DE)

( * ) Notice: Subject to any disclaimer, the term of this patent is extended or adjusted under 35 U.S.C. 154(b) by 8 days.

(21) Appl. No.: 13/225,929

(22) Filed: Sep. 6, 2011

(65) Prior Publication Data

US 2011/0316178 A1 Dec. 29, 2011

Related U.S. Application Data

(60) Continuation of application No. 12/273,144, filed on Nov. 18, 2008, now abandoned, which is a division of application No. 11/065,237, filed on Feb. 24, 2005, now Pat. No. 7,452,500.

(30) Foreign Application Priority Data

Feb. 25, 2004 (DE) .......................... 10 2004 009 127

(51) Int. Cl.
*B23K 26/00* (2006.01)
*B23K 15/00* (2006.01)

(52) U.S. Cl.
USPC ................... 219/121.17; 219/121.66; 419/53; 156/62.2; 156/272.2; 264/497

(58) Field of Classification Search
USPC . 156/62.2, 272.2, 272.8; 219/121.13–121.17, 219/121.35, 121.63–121.66, 121.85; 264/113, 264/125, 497; 419/53, 31
See application file for complete search history.

(56) References Cited

U.S. PATENT DOCUMENTS

| | | | |
|---|---|---|---|
| 4,711,823 A | 12/1987 | Shiina | |
| 4,839,493 A | 6/1989 | Herziger et al. | |
| 4,863,538 A | 9/1989 | Deckard | |
| 5,017,551 A * | 5/1991 | Agostinelli et al. | .......... 505/235 |
| 5,202,545 A | 4/1993 | Hoffmann et al. | |
| 5,352,405 A | 10/1994 | Beaman et al. | |
| 5,393,482 A | 2/1995 | Benda et al. | |
| 5,427,733 A | 6/1995 | Benda et al. | |

(Continued)

FOREIGN PATENT DOCUMENTS

| | | |
|---|---|---|
| DE | 196 49 965 | 12/1996 |
| DE | 199 35 274 | 7/1999 |
| WO | WO 01/81031 A1 | 11/2001 |

*Primary Examiner* — Samuel M Heinrich
(74) *Attorney, Agent, or Firm* — Altera Law Group, LLC

(57) ABSTRACT

The invention relates to a method for making metallic and/or non-metallic products 2, in particular dental products, by freeform sintering and/or melting, in which the products 2 are fabricated layer by layer from a material 5 that is applied layer by layer by means of a computer-controlled high-energy beam 7, in particular a laser or electron beam. In order to reduce production times, beam 7 irradiates predetermined positions P1 to P6 of a layer of a material 5 a plurality of time, namely m times, where m is a whole integer greater than 1. Each of said positions P1 to P6 is initially heated during the first irradiation to a temperature below the melting point $T_{melt}$ of the material 5, and during the mth irradiation to a temperature above said melting point and is completely melted over the entire thickness of the layer in such a way that the material (5) fuses at said position to the layer thereunder. The invention also relates to an apparatus for performing said method.

9 Claims, 4 Drawing Sheets

U.S. PATENT DOCUMENTS

| | | |
|---|---|---|
| 5,508,489 A | 4/1996 | Benda et al. |
| 5,640,667 A | 6/1997 | Freitag et al. |
| 5,876,550 A * | 3/1999 | Feygin et al. ............. 156/264 |
| 5,904,890 A * | 5/1999 | Lohner et al. ............. 264/401 |
| 5,908,569 A | 6/1999 | Wilkening et al. |
| 6,007,764 A * | 12/1999 | Benda et al. ............. 419/7 |
| 6,215,093 B1 | 4/2001 | Meiners et al. |
| 6,305,769 B1 | 10/2001 | Thayer et al. |
| 6,333,484 B1 * | 12/2001 | Foster et al. ............. 219/121.64 |
| 6,503,310 B1 | 1/2003 | Sullivan |
| 6,555,779 B1 | 4/2003 | Obana et al. |
| 7,107,118 B2 | 9/2006 | Orozco et al. |
| 2003/0201255 A1 | 10/2003 | Manetsberger et al. |
| 2004/0228754 A1 | 11/2004 | Abe et al. |

* cited by examiner

METHOD AND APPARATUS FOR MAKING PRODUCTS BY SINTERING AND/OR MELTING

The invention relates to a method for making metallic and/or non-metallic products, in particular dental products, by freeform sintering and/or melting, in which the products are fabricated layer by layer from a material that is applied layer by layer by means of a computer-controlled high-energy beam, in particular a laser or electron beam.

The invention also relates to an apparatus for performing such a method, said apparatus comprising: a beam source for generating said beam, a platform for receiving a material that can be applied in layers, and a controller for controlling the beam, by means of which the beam can be guided by computer control to fabricate the products layer by layer from the material.

Such methods and apparatus are known. They are used, inter alia, to make dental products such as crowns, bridges, implants, etc., but they are also used in other fields of application.

However, due to the high degree of precision required for the products being made, these known devices are very complex in design and therefore very costly, but the unit costs for the products can be reduced if the time required to make a product is shortened. In this way, it is possible to increase the efficiency of such a device.

The invention is therefore focused on the technical problem of reducing the production time required to make products by freeform sintering and/or melting.

The invention solves this problem with a method of the kind initially specified by configuring the control unit in such a way that by means of said control unit the beam irradiates predetermined positions of a material a plurality of times in each case, namely m times, where m is a whole integer greater than 1, wherein each of said positions is initially heated during the first irradiation to a temperature below the melting point of the material and during the m-th irradiation to a temperature above said melting point so that it is completely melted over the entire thickness of the layer in such a way that the material fuses at said position to the layer thereunder.

The invention also solves the problem by means of an apparatus of the kind initially specified, in which the controller is configured in such a way that the beam can be controlled by means of said controller in the manner described in the foregoing.

The invention is based on the realization that the production time can be reduced when the energy of the high-energy beam is coupled into the material in a plurality of steps. In the first step, the energy is coupled into a certain position in the layer of material until the respective portion of the layer at said position has been heated to a temperature just below its melting point. In the final step of coupling in energy, the beam then heats said portion above the melting point, thereby fusing the material to the layer below it. In this way, the product being made is formed.

When melting and/or sintering using a high-energy beam, it is important that every portion covered by the beam is brought to the melting point of the material, but without exceeding the vaporization point, since otherwise the material would merely vaporize without forming the product being made.

However, the beam reaches only a surface portion of the layer of material being irradiated. For this reason, only the surface of the irradiated portion is heated at first. The side of said portion facing away from the beam is not reached, however. Thus, the side facing away from the beam is heated solely by heat transfer within said portion. This limits the maximum processing speed.

The invention overcomes this limitation by irradiating each position several times so that heat transfer from the hot to the cold side can occur within the respective portion of the layer of material during a period in which the surface of said portion is not being irradiated. Said duration can then be used to heat another portion of the layer. After said other portion has been heated, the beam returns to the former portion and can continue or complete the heating process.

Such alternating irradiation means there is no need to wait during irradiation for time-consuming temperature equalization to occur within the irradiated portion. Instead, these temperature equalizations can occur after an irradiation step has temporarily ended and another irradiation step is started or continued elsewhere.

In this way, the durations of irradiation at separate positions or portions of the material are significantly reduced. This alternating irradiation also allows the beam source, e.g. a laser or electron beam source, to be higher powered, thus allowing a greater amount of energy to be delivered to the respective position. The risk of explosive vaporization of these particles of material is considerably reduced by directing the beam to a different position after a short period.

In one particularly preferred embodiment, the positions in a layer of material to be irradiated are irradiated twice. Each of these positions is initially irradiated for a first duration, then not irradiated for a second duration. The second duration, of non-irradiation, is at least exactly as long or twice as long as the first duration of irradiation.

In another preferred embodiment, the positions in a layer of material to be irradiated are irradiated three times. In this case, each of these positions is initially irradiated for a first duration, then not irradiated for a second duration. This process is then repeated at that position. Finally, a third irradiation step of the first duration is performed. In each case, the second duration, of non-irradiation, is at least exactly as long, twice as long or four times as long as the first duration of irradiation.

In one particularly preferred embodiment, the beam is guided backward and forward with a first substantially linear movement, with the forward movement extending over a longer path than the backward movement. This results in simple alternation between irradiation and non-irradiation of adjacent positions.

It is preferred that a second, meandering movement be superimposed upon the first movement. In this way, surface portions of the product being made are formed very uniformly.

In yet another preferred embodiment, an ensuing or completed contour of the product (2) is optically measured during and/or after a layer is irradiated. The measuring data thus obtained are compared with specified data, and if a deviation is discovered the beam is adjusted to take account of the deviation. In this way, the precision and dimensional accuracy of the products being made can be further improved.

Other preferred embodiments derive from the embodiments that are described in detail with reference to the enclosed drawings. In the drawings, FIG. 1 is a schematic sectional view of an apparatus for making products by freeform laser sintering and/or melting in accordance with one embodiment of the invention;

Figure 1:
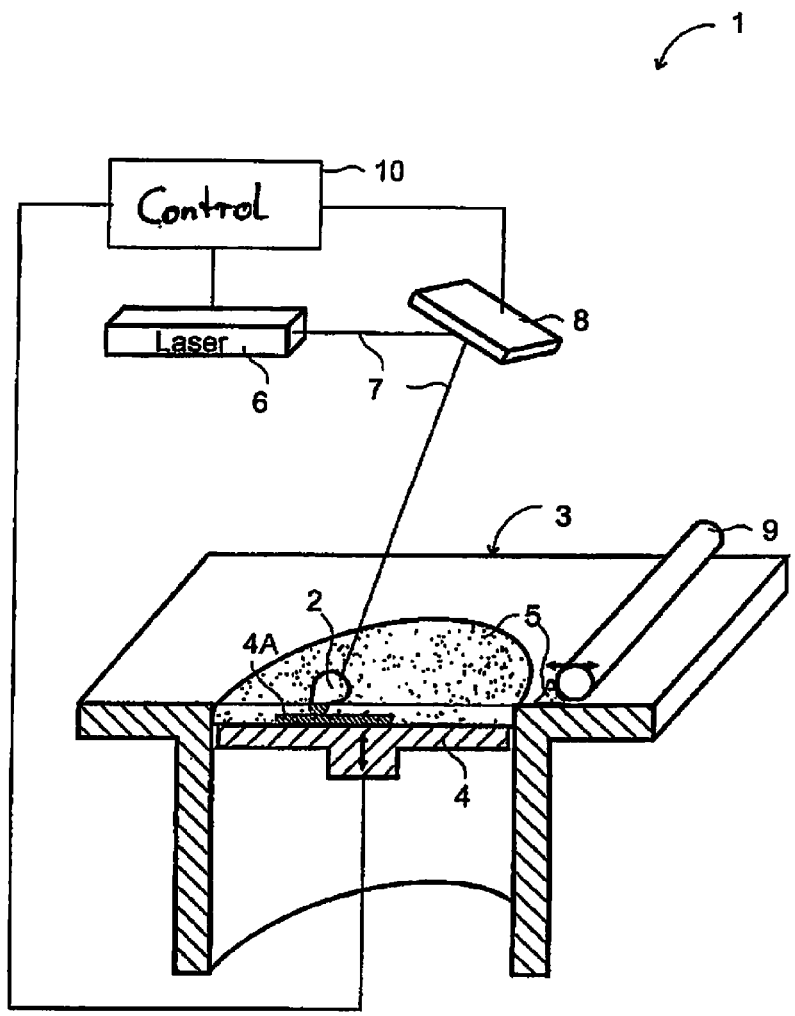

FIG. 1 shows an apparatus 1 for making metallic and/or non-metallic products 2, in particular dental products such as crowns, bridges, implants etc., using freeform laser sintering and/or melting. Apparatus 1 has a table 3 with a vertically adjustable platform 4 on which a substrate 4A lies. Platform 4 can be adjusted stepwise in height by means of a drive, not shown, in particular in steps adapted to the size of powder grains of a material 5 which is present in powdery form.

Apparatus 1 also has a laser 6 disposed above table 3, for example a $CO_2$ laser, beam 7 of which is guided through a suitable device, in particular a computer-controlled reflecting galvanometer 8.

Apparatus 1 also has a coating mechanism 9 by means of which the powdery material 5 is uniformly distributed over the surface of table 3, such that the space between the surface of platform 4 and the surface of table 3 is filled with powdery material 5.

A product 2 is now made in the following way: first of all, platform 4 is in an upper starting position. Laser 6 is then activated and its laser beam 7 is directed onto the powdery material 5. Owing to the heat it generates, laser beam 7 solidifies and melts the powdery material 5, which is then, depending on the intensity of energy applied to the powdery material 5, either sintered or fused to surrounding grains of powder. In accordance with a preprogrammed shape for the product 2 being made, i.e. by means of computer control, laser beam 7 irradiates predetermined positions of the powdery material 5. A layer of fused or sintered material is produced at the portions irradiated by laser beam 7.

As soon as a layer has been completed, the laser 6 is deactivated and platform 4 is lowered by one layer that is adapted, for example, to the average diameter of the powder grains in the material 5. Using coating mechanism 9, a new layer of powdery material 5 is applied and smoothed. Laser 6 is then reactivated, and the computer-controlled laser beam 7 again moves to predetermined computer-controlled positions within which the powdery material 5 is to be fused or sintered with the previously produced layer, or also to adjacent or non-adjacent areas. This process of applying layers of powdery starting material 5 and sintering or fusing said layers with the previously applied layers using a laser beam 7 is performed repeatedly until the product 2 has been formed with the desired shape.

Apparatus 1 includes a controller 10 for controlling, in particular, the activation and deactivation of laser 6, the positioning of laser beam 7 via mirror galvanometer 8, as well as the vertical adjustment of platform 4. The coordination of these components of apparatus 1 ensures the desired configuration of the products 2.

Controller 10 generates its commands in accordance with previously stored model data of the product, on the one hand. Controller 10 also generates commands according to measuring data obtained by optically measuring an ensuing or completed contour of product 2 during and/or after irradiation of a layer. These measuring data are compared with specified data by controller 10. If a deviation between the specified data and the measured data is discovered in this comparison, laser beam 7 is adjusted by controller 10 to take account of such deviation, by controlling the laser 6 and the mirror galvanometer 8 accordingly.

The laser beam 7 is extremely concentrated in order to reach a high energy density. The laser beam 7 therefore hits material 5 at a discrete point. However, any such "point" extends over a certain area of the surface.

Figure 2:
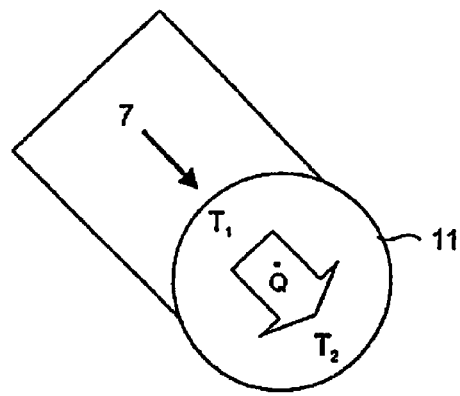
FIG. 2 is a schematic view illustrating the coupling in of heat and the temperature equalization process inside a grain of the powdery material during laser sintering or melting.

FIG. 2 shows, in a highly magnified view, how laser beam 7 hits a grain 11 of the powdery material 5. In laser sintering or laser welding, a large number of powder grains 11 applied in layers must be completely melted and fused with the layer underneath. To achieve this, each position within grain 11 must reach the melting point of the material without exceeding the vaporization point.

The incident laser beam 7 heats the surface of powder grain 11, but the side of grain 11 facing away from laser beam 7 is not reached directly by the laser radiation. This side facing away from the beam is therefore heated solely by heat transfer $\dot{Q}$ inside powder grain 11. A powder grain 11 thus has two places with extreme temperatures, namely a first high temperature $T_1$ on the side facing the laser beam 7 and a comparatively low temperature $T_2$ on the side of powder grain 11 facing away from laser beam 7.

As already explained in the foregoing, low temperature $T_2$ must also reach the melting point of the material. While this is happening, however, the high temperature $T_1$ must not exceed the vaporization point. Due to the heat transfer $\dot{Q}$ inside the powder grain 11, there is a maximum permissible temperature differential $T_1$-$T_2$ limiting the maximum processing speed.

Figure 3:
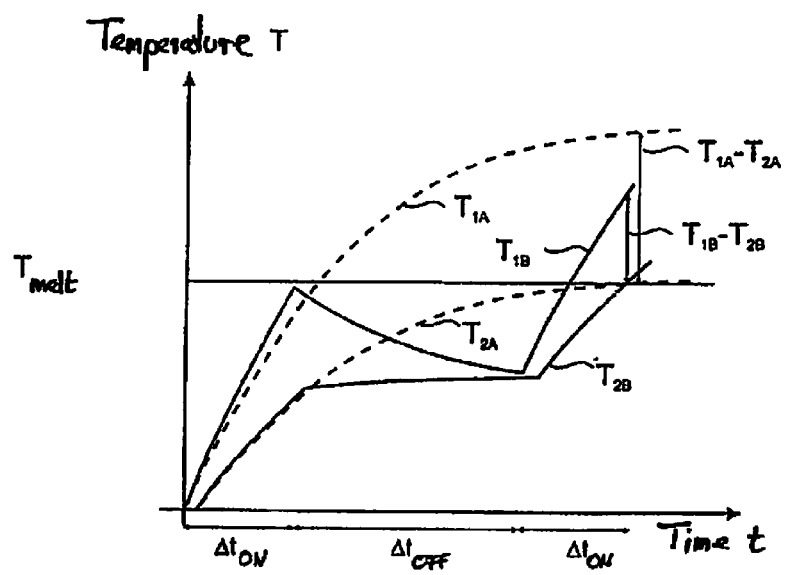
FIG. 3 is a diagram showing the temperature change over time at or in the grain of powder on the side facing a laser beam and on the side facing away from the laser beam for two different irradiation strategies.

FIG. 3 shows, for two irradiation strategies (A and B), the temperature curves for a powder grain on the side facing and the side facing away from laser beam 7.

The first irradiation strategy (A) is shown with broken lines and corresponds to the conventional procedure. Curve $T_{1A}$ for temperature over time traces the temperature on the side of powder grain 11 facing the laser beam. Likewise, temperature curve $T_{2A}$, traces the temperature on the side facing away from the laser beam. Powder grain 11 is completely melted when both temperature $T_{1A}$ and temperature $T_{2A}$ have exceeded the melting point $T_{melt}$. Once said melting point has also been exceeded on the side of the powder grain facing away from the laser beam, the next position can start to be melted.

A second irradiation strategy (B) is shown with solid lines in FIG. 3. This irradiation strategy corresponds to an embodiment of the present invention. Temperature curve $T_{1B}$ traces the temperature on the side of powder grain 11 facing laser beam 7, whereas temperature curve $T_{2B}$ traces the temperature on the side of powder grain 11 facing away from laser beam 7.

Laser beam 7 is initially switched on for a duration $\Delta t_{on}$. The side of powder grain 11 facing laser beam 7 begins to heat up to a temperature below the melting point $T_{melt}$. The laser beam is then no longer focused on this position, with the result that no more energy is coupled into said position. The duration over which no energy is coupled in, or that this position is not irradiated, is marked $\Delta t_{off}$ in FIG. 3. The laser beam is then directed to the same position again, with the result that energy is again coupled into it, thus leading to a rapid increase in temperature $T_{1B}$ over a duration $\Delta t_{on}$. A short time later, the temperature on the side of powder grain 11 facing the laser beam likewise rises considerably until melting point $T_{melt}$ is reached.

Thus, in this strategy according to the invention, a position on the powder layer is irradiated a succession of times such that during the period of non-irradiation a temperature equalization process occurs inside the previously irradiated particle of material, and during said period a different position of the powder layer can be irradiated. By applying this irradiation strategy, the temperature difference $T_{1B}$-$T_{2B}$ is reduced relative to the temperature difference $T_{1A}$-$T_{2A}$, in particular when a powder grain is fully melted. Owing to this reduced temperature difference, a higher-powered laser can be used so that the production time can be shortened. In addition, other points can start to be heated during the $\Delta t_{off}$ period. The overall result is that production times are considerably shortened. Another advantage of this irradiation strategy is that explosive vaporization of smaller powder grains can be avoided, since the duration that the laser beam remains at single positions is substantially shorter than is the case with the conventional irradiation strategy (A).

Figure 4:
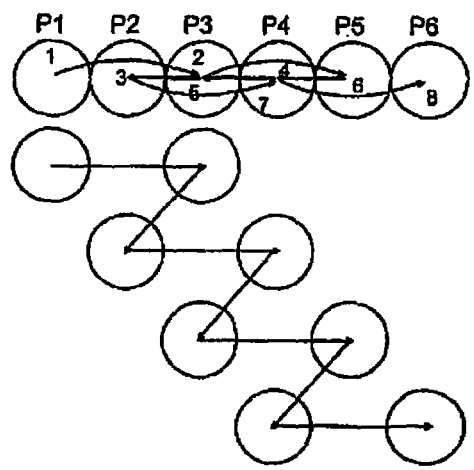
FIG. 4 is a possible path that a laser beam is guided along to irradiate predetermined positions.

FIG. 4 illustrates how the laser beam is guided along predetermined positions P1, P2, P3, P4, P5 and P6. The laser beam is firstly directed at position P1 for duration $\Delta t_{on}$. The laser beam is then directed at P3, the next position but one, in order to heat said position likewise for a duration $\Delta t_{on}$. The laser beam is subsequently brought back to irradiate position P2 between positions P1 and P3. The laser beam remains there for the same duration $\Delta t_{on}$. The laser beam then skips position P3 and is directed at the following position P4, again for duration $\Delta t_{on}$. After that, the laser beam returns to position P3 and stays at said position P3 for a further duration $\Delta t_{on}$.

It can be seen that the laser beam irradiates position P3 twice, each time for duration $\Delta t_{on}$, and that said position is not irradiated during period $\Delta t_{off}$, which is substantially twice as long as duration $\Delta t_{on}$.

However, the invention is not limited to this particular irradiation strategy, but rather includes other irradiation strategies as well.

Figure 5:
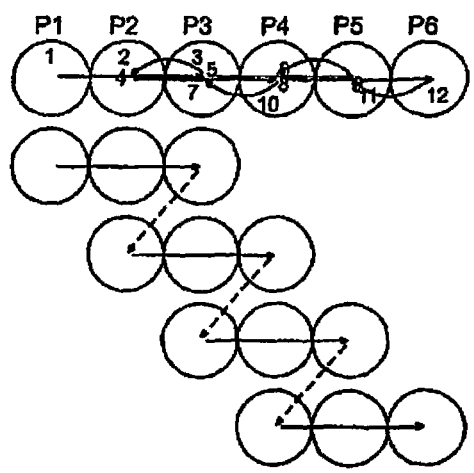
FIG. 5 is another possible path that a laser beam is guided along to irradiate predetermined positions.

FIG. 5 shows another irradiation strategy in which each single position is irradiated three times. Irradiation is performed here in the sequence P1, P2, P3, P2, P3, P4, P3, P4, P5, P4, P5, P6, . . . .

In this irradiation strategy, the duration of non-irradiation between two irradiation steps at the same position is substantially of exactly the same length as the duration of irradiation at the single positions.

Figure 6:
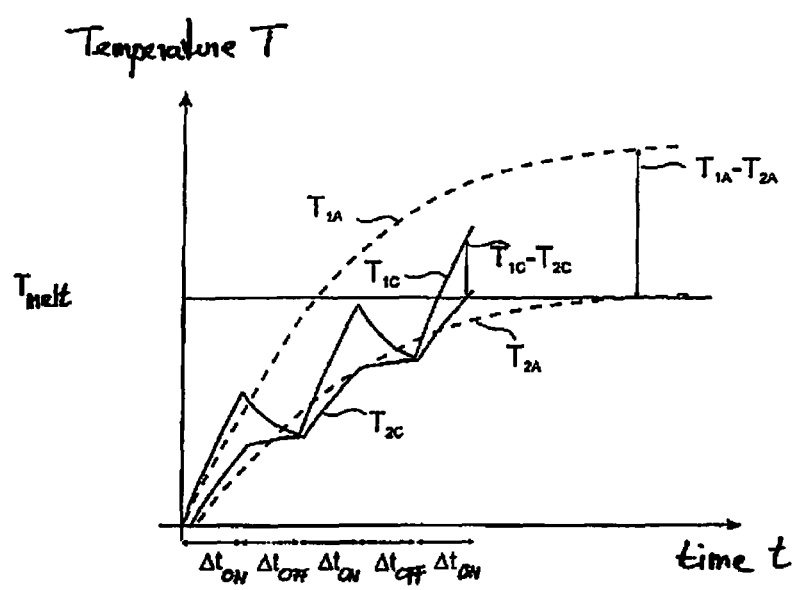
FIG. 6 is another diagram illustrating the temperature change over time at or in the grain of powder on the side facing a laser beam and on the side facing away from the laser beam for two different irradiation strategies.

FIG. 6 shows the corresponding temperature curves $T_{1C}$ and $T_{2C}$ analogous to FIG. 3. In order to show the contrast, the temperature curves $T_{1A}$ and $T_{2A}$ for a single irradiation step at each separate position are shown in broken lines (irradiation strategy A).

However, the solid lines in FIG. 6 show that a first temperature below the melting point $T_{melt}$ is reached during a first irradiation period $\Delta t_{on}$. Although the temperature at the respective position increases during a second irradiation step lasting $\Delta t_{on}$, it is only to a temperature just below the melting point $T_{melt}$. It is not until a third irradiation step that both temperature $T_{1B}$ and temperature $T_{2B}$ exceed the melting point $T_{melt}$, such that the respective position on the powdery material is fully melted.

FIGS. 4 and 5 show the beam (4) moving backward and forward with a substantially linear movement, the forward movement extending over a longer path than the backward movement. However, since the products being made are usually comprised not only of very thin linear contours, a second, meandering movement is superimposed upon these linear movements of the laser beam. Said meandering movements serve in particular to produce broader structures as well, i.e. structures that are broader in extension than the diameter of the laser beam.

Additional movements can be superimposed upon said first linear and said second meandering movements in order to produce more complex contours on the product being made.

Owing to the multiple irradiation of each single position along a predetermined laser beam path, the invention enables production times to be reduced considerably, since energy is effectively supplied to several positions simultaneously. In addition, due to the temperature equalization between two irradiation steps, a higher-powered laser can also be used quite easily without explosive vaporization, particularly of smaller powder grains, occurring. The invention thus permits the efficient exploitation of devices for freeform laser sintering and/or melting.

Although the invention was described in the foregoing in connection with laser sintering and laser melting, it is not restricted to using a laser beam for sintering or melting. An electron beam, for example, may be used instead of a laser beam. For this reason, the laser described above can easily be replaced by an electron beam source. In general, therefore, the invention relates to any kind of sintering and/or melting process effected by a high-energy beam from a suitable source for such a high-energy beam.

The invention claimed is:

1. An apparatus for making metallic and/or non-metallic products, by freeform melting using a high-energy beam, wherein the apparatus comprises:
   a beam source for generating said beam,
   a platform for receiving a powder material that can be applied in layers and a controller for controlling the beam, by means of which the beam can be guided by computer control in order to fabricate the products layer by layer from the material, wherein the controller is configured in such a way that, by means of said controller, the beam irradiates predetermined positions of the material a plurality of m times, where m is a whole integer greater than 1, wherein each of said positions is initially heated during the first irradiation to a temperature below the melting point ($T_{melt}$) of a single grain of the powder material and during the mth irradiation to a temperature above said melting point ($T_{melt}$) and wherein the powder grains are completely melted over the entire thickness of the layer in such a way that the powder grains of the material fuse at said position to the layer thereunder.

2. Apparatus according to claim 1, wherein m equals 2.

3. Apparatus according to claim 1, wherein the controller is adapted to irradiate each of said positions for a first duration ($\Delta t_{on}$), then not irradiate during a second duration ($\Delta t_{off}$), wherein the second duration ($\Delta t_{off}$) is at least exactly as long or twice as long as the first duration ($\Delta t_{on}$).

4. Apparatus according to claim 1, wherein m equals 3.

5. Apparatus according to claim 4, wherein the controller is adapted to irradiate each of said positions for a first duration ($\Delta t_{on}$), then not irradiate during a second duration ($\Delta t_{off}$), wherein the second duration ($\Delta t_{off}$) is at least exactly as long, twice as long or four times as long as the first duration ($\Delta t_{on}$).

6. Apparatus according to claim 1, wherein the controller is configured to guide the beam backward and forward with a first substantially linear movement, the forward movement extending over a longer path than the backward movement.

7. Apparatus according to claim 6, wherein the controller is configured to superimpose a second, meandering movement upon said first substantially linear movement.

8. Apparatus according to claim 1, wherein the high energy beam is a laser or electron beam.

9. Apparatus according to claim 1, further comprising an optical measuring device for measuring the contour of the product, wherein the controller is configured to compare the measured data of said optical measuring device with specified data and to adjust the beam if a deviation is discovered to take account of the deviation thus identified.

* * * * *